United States Patent [19]

Roos et al.

[11] Patent Number: 5,175,305

[45] Date of Patent: Dec. 29, 1992

[54] PROCESS FOR PREPARING N,N'-BIS(TETRABROMOPHTHALIMIDE)

[75] Inventors: Joseph W. Roos; Robert M. Moore, Jr., both of Baton Rouge, La.

[73] Assignee: Ethyl Corporation, Richmond, Va.

[21] Appl. No.: 743,705

[22] Filed: Aug. 12, 1991

Related U.S. Application Data

[62] Division of Ser. No. 530,112, May 29, 1990, Pat. No. 5,076,970.

[51] Int. Cl.$^5$ .......................................... C07D 403/04
[52] U.S. Cl. .................................................. 548/461
[58] Field of Search ........................................ 548/461

[56] References Cited

U.S. PATENT DOCUMENTS 4,720,553  1/1988  Lee et al. ............................. 548/475
4,894,187  1/1990  Bonnet et al. ....................... 252/609

Primary Examiner—Joseph Paul Brust
Assistant Examiner—Jacqueline Haley
Attorney, Agent, or Firm—David E. LaRose; Edgar E. Spielman, Jr.

[57] ABSTRACT

This invention relates to a process for preparing and treating a product predominant in N,N'-bis(tetrabromophthalimide) so as to produce a bisimide product which has enhanced suitability for use in thermoplastic formulations as a result of reduction in volatile impurities and particle size.

13 Claims, No Drawings

PROCESS FOR PREPARING N,N'-BIS(TETRABROMOPHTHALIMIDE)

This application is a division of application Ser. No. 07/530,112, filed May 29, 1990, now U.S. Pat. No. 5,076,970.

BACKGROUND OF THE INVENTION

This invention relates to a process for preparing a thermally stable flame retardant product which is predominant in the bisimide,

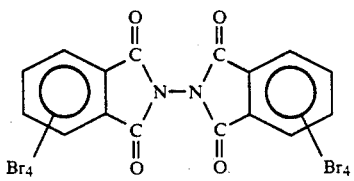

N,N'-bis(tetrabromophthalimide) predominant products have been found to be useful flame retardants in polyesters, e.g. polybutylene terephthalate, and other resin formulations.

While various processes have been described for the preparation of such bisimide predominant products, almost all produce a product which contains significant amounts of volatile impurities, which impurities contribute to the product's lack of good thermal stability. See, for example, the process of Bonnet et al. U.S. Pat. No. 4,894,187 wherein a N,N'-bis-(tetrabromophthalimide) product is produced which contains up to 80% by weight of a substantially equimolar amount of the impurities, tetrabromophthalic anhydride and N-aminotetrabromophthalimide. The tetrabromophthalic anhydride impurity is especially troublesome as it volatilizes at polymer processing temperatures.

THE INVENTION

This invention provides a process for enhancing the suitability of a bisimide product for use in thermoplastic formulations the bisimide product being predominant in N,N'-bis(tetrabromophthalimide) and containing, as an impurity, tetrabromophthalic anhydride. The process comprises: contacting the bisimide product with an aqueous basic solution; and removing at least a portion of any reaction products produced by the contacting to yield, as a remainder, the bisimide product having said enhanced suitability.

The process of this invention enhances the suitability of the so treated bisimide product by (1) reducing the volatile impurity content of the bisimide product and (2) reducing the average particle size of the bisimide product. The former results in a more thermally stable bisimide product and thus one which is more acceptable in the work environment. The latter is important as a smaller particle size helps insure even distribution of the bisimide product in a thermoplastic formulation. Even distribution is important as maximization of the flame retardant property in the thermoplastic formulation is achieved.

The process of this invention may be performed on the bisimide product at any point during its production which is after completion of the bisimide forming reaction. For example the process of this invention can be practiced on the bisimide product before it is separated from the reaction mass in which it was formed, during its separation from the reaction mass, and after its separation from the reaction mass. The process can be performed on a bisimide product after it has undergone post separation treatment, e.g. drying etc. It is preferred to treat the bisimide product after it has been separated from the reaction mass and is in the form of a wet cake. For example when the bisimide product is separated from the reaction mass by centrifugation, the resultant wet cake can be contacted with the aqueous basic solution before discharge of the wet cake from the centrifuge. In a particularly preferred embodiment, the wet cake is washed with water in the centrifuge prior to contacting it with the aqueous basic solution.

If the process of this invention is performed on a fully recovered dry product, an aqueous slurry of the product can be prepared which is then contacted with the aqueous basic solution.

In the process of this invention, the aqueous basic solution may be any basic solution compatible with N,N'-bis(tetrabromophthalimide), such as NaOH, KOH, NH$_4$OH, Na$_2$CO$_3$ solutions and the like. Particularly preferred is a NH$_4$OH solution. The basic solution may also be provided by bubbling gaseous ammonia through an aqueous slurry containing the bisimide product.

The bisimide product is contacted with an amount of the aqueous basic solution and for a period of time which are sufficient to obtain the enhancement sought for the bisimide product. A convenient method for determining the sufficiency of the contacting is to monitor the drop in the acid number, expressed as milligrams (mg) of KOH per gram (g) of bisimide product neutralized, during the contacting period. A drop in the acid number of about 40% or greater will signify a substantial reduction in the tetrabromophthalic anhydride content and thus a generally significant increase in the thermal stability of the bisimide product. For bisimide products of the type described in U.S. Pat. No. 4,894,187 which contain tetrabromophthalic anhydride and N-aminoimide in equimolar and in significant amounts, a reduction in the acid number of from about 50% to about 90% will be indicative of suitable contact between the aqueous basic solution and the bisimide product. Since enhancement of the bisimide product, in accordance with this invention, is obtained for any increase in thermal stability and/or any average particle size reduction, the above percentages for the acid number drop represent preferred drops and are not to be taken as absolute requirements to be achieved to obtain any of the benefits of this invention. For example, an acid number drop of 10% or 20% may not be as significant as the above larger acid number drops, but that should not lead to a conclusion that no increase in thermal stability and/or reduction in average particle size is achieved. On the contrary, in some cases, small drops in the acid number may be indicative of just the particular enhancement of suitability sought for a particular bisimide product treated.

After contacting the bisimide product with the aqueous basic solution, the so contacted bisimide product is recovered after separating at least a portion of any of the reaction products produced by the contacting from the so contacted bisimide product. The reaction products are predominantly the reaction products of tetrabromophthalic anhydride and the aqueous basic solution. Removal of the reaction products from the so contacted bisimide product can be accomplished by conventional means, such as washing of the contacted bisimide product with water followed by a liquid-solid separation technique, e.g. decantation, settling, filtration, centrifugation and the like.

The remaining bisimide product is then dried by conventional means. The dry bisimide product will be of a particle size which will not require performance of subsequent size reduction techniques, e.g. grinding, milling, etc. or will only require the use of such techniques to an extent which is less that that which would normally be required.

The dry product may contain other impurities, such as N-aminoimide, which-are less likely to adversely affect the thermal stability of the bisimide product as such impurities are present in very small amounts or are less volatile than tetrabromophthalimide. The N-aminoimide impurity may be represented by the following formula:

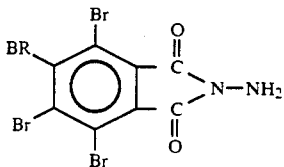

In another embodiment of the invention, a product predominant in N,N'-bis(tetrabromophthalimide) and having non-equimolar amounts of tetrabromophthalic anhydride and N-aminoimide as impurities is produced by: a) forming a reaction mass from at least (i) tetrabromophthalic anhydride, (ii) hydrazine or a hydrazine provider compound, and (iii) a reaction medium selected from a concentrated sulfuric acid medium, an oleum medium, and an aqueous medium; (b) maintaining the so-formed reaction mass at a temperature within the range of from about 40° C. to about 300° C. for a time sufficient to obtain a product predominant in N,N'-bis(tetrabromophthalimide) and having substantially equimolar amounts of tetrabromophthalic anhydride and N-aminoimide; (c) separating the product from the reaction mass; and (d) contacting the product with an aqueous basic solution.

The tetrabromophthalic anhydride used in the process of this invention can be obtained in a very pure form, e.g. 99+% pure from Ethyl Corporation as Saytex RB-49 flame retardant.

The hydrazine component used in forming the reaction mass can be supplied by hydrazine itself or by hydrazine providing compound, i.e., a hydrazine salt, hydrate, etc. which, in the reaction mass environment, will provide hydrazine. Suitable hydrazine providing compounds are hydrazine sulfate, hydrazine hydrate, hydrazine monohydrate, hydrazine dihydrochloride, hydrazine monohydrochloride, hydrazine tartrate, hydrazine acetate, and hydrazine bisulfate. Mixtures of various hydrazine salts, i.e. hydrates, sulfates, acetates, tartrates, hydrochlorides, etc., may also be used. Preferred is hydrazine sulfate.

In a particularly preferred embodiment of the invention, concentrated sulfuric acid is used as the reaction medium. When used as the reaction medium, it is generally a 90 to 100% sulfuric acid medium. The commercially available concentrated acids are preferred, e.g. those falling within the range of 93 to 100% sulfuric acid. Some specific examples are, 93%, 96%, 98-99% and 100% sulfuric acid.

In forming the reaction mass, it is convenient to first charge a reaction vessel with a solution of tetrabromophthalic anhydride and a first portion of concentrated sulfuric acid and then adding, to this so-charged solution, a solution comprised of the hydrazine component and a second portion of concentrated sulfuric acid. The first and second portions of concentrated sulfuric acid substantially equal the total acid used in forming the reaction mass. Generally, the first portion will comprise 40% to 60% of the total amount of concentrated sulfuric acid used. In another preferred method of formation, the same solutions are used but the order of addition is reversed. While these methods are preferred, other techniques can be used to form the reaction mass. For example, the hydrazine component can be added neat to a solution comprised of the tetrabromophthalic anhydride and all of the concentrated sulfuric acid to be used in forming the reaction mass.

The total amount of sulfuric acid used in forming the reaction mass is within the range of from about 5 to about 50 moles of acid per mole of tetrabromophthalic anhydride. A preferred amount is within the range of from about 8 to about 12 moles per mole of tetrabromophthalic anhydride.

When an aqueous medium is used in forming the reaction mass it will be used in the same manner and in the same amounts as are taught for the N,N'-bis(tetrabromophthalimide) process of U.S. Pat. No. 4,894,187, which is incorporated herein, for their teachings, as if fully set forth. As taught in U.S. Pat. No. 4,894,187, the aqueous medium may be comprised of water and minor amounts of acid.

When concentrated sulfuric acid is used as the reaction medium, the reaction mass is formed at a temperature within the range of from about 80° C. to about 270° C. and preferably within the range of from about 180° C. to about 230° C. It is preferred that the molar ratio of tetrabromophthalic anhydride to the hydrazine or hydrazine providing compound used in forming the reaction mass be from about 1:0.6 to about 1:0.9. These ratios provide an excess over the stoichiometric ratio of 1:0.5, which excess provides sufficient amount of hydrazine to react with substantially all of the tetrabromophthalic anhydride. To obtain as pure a product as is possible at the highest yield, the practitioner should adjust this ratio so that the amount of unreacted hydrazine and tetrabromophthalimide anhydride is minimized. It is possible to use a stoichiometric deficiency or excess of tetrabromophthalic anhydride and still produce a N,N'-bis(tetrabromophthalimide) product, however, the obtained product will contain, respectively, monoimides of hydrazine and/or tetrabromophthalic anhydride.

After the reaction mass has been substantially formed, the reaction mass is maintained at a temperature within the range of from about 110° C. to about 300° C., and preferably maintained at a temperature within the range of from about 180° C. to about 230° C. until the reaction is substantially complete. The reaction mass may be maintained at the selected temperature for a period up to about 20 hours and preferably from about 6 to about 14 hours in order to substantially complete the reaction. This period is shorter when using the higher temperatures and longer when using the lower temperatures.

The process pressure is preferably atmospheric, however, sub-atmospheric and superatmospheric pressures can be used provided that care is taken to prevent loss of any of the major constituents of the reaction mass.

Subsequent to this period, the bisimide product is separated from the reaction medium and is in the form of a wet cake. The wet cake is then washed with a washing medium to remove residual sulfuric acid from the wet cake. After washing, the wet cake is treated by contacting the wet cake with an amount of an aqueous NH$_4$OH solution sufficient to obtain a reduction in the acid number of the so treated bisimide product. It is highly desirable to obtain a reduction in the acid number of the so treated bisimide product of about 40% or greater in order to significantly increase the thermal stability of the bisimide product.

As in the case for the first described embodiment of the invention, the second embodiment results in the reduction of the amount of volatile impurities in the product and, surprisingly, a reduction in the average particle size. Since the particles have a smaller size, less milling or grinding will be required to meet particle size specifications. Typically the average particle size of the bisimide product produced by the process of this invention is less than about 6 microns and at least about 99% of the particles are typically less than about 16 microns. The particle size may vary however, depending on the average size particles produced prior to the contacting step.

The enhanced bisimide product is further characterized in that it has a non-equimolar mixture of the impurities tetrabromophthalic anhydride and N-aminoimide. On a molar ratio basis, the bisimide product may have a ratio of from about 1.5:1 to about 100:1 moles of N-aminoimide per mole of tetrabromophthalic anhydride. Typically, the molar ratio of N-aminoimide to tetrabromophthalic anhydride ranges from about 2:1 to about 10:1 as a result of the process of this invention.

After treating the wet cake with the aqueous NH$_4$OH solution, the wet cake is filtered to recover the solids. Removal of residual aqueous NH$_4$OH solution from the filtered solids can be accomplished by again washing the solids with a washing medium. The washing medium, which is used before and after the contacting step, is preferably water, but other mediums such as methanol, acetone, ethanol may be used.

Subsequent to washing the solids to remove residual aqueous NH$_4$OH solution, the solids are dried to remove any remaining washing medium. The filtration, washing, contacting, rinsing, and drying steps are all done conventionally.

The equipment in which the process of this invention is carried out should be of materials which can withstand the corrosive nature of the compounds with which it may come into contact. For example, glass-lined equipment is especially suitable for the process of this invention.

The bisimide products obtained in accordance with the processes of this invention are particularly well suited as a flame retardant in plastics of all kinds. These bisimide products may be used as a flame retardant in formulation with virtually any flammable material. The material may be macromolecular, for example, a cellulosic material or a polymer. Illustrative polymers are: olefin polymers, cross-linked, and otherwise, for example, homopolymers of ethylene, propylene, and butylene; copolymers of two or more of such alkylene monomers, and copolymers of one or more of such alkylene monomers, and any other copolymerizable monomoners, for example, ethylene/propylene copolymers, ethylene/ethyl acrylate copolymers, and ethylene/vinyl acetate copolymers; polymers of olefinically unsaturated monomers, for example, polystyrene, e.g. high impact polystyrene, and styrene copolymers; polyurethanes; polyamides; polyimides; polycarbonates; polyethers; acrylic resins; polyesters, especially poly(ethyleneterephthalate) and poly(butyleneterephthalate); epoxy resins; alkyl resins; phenolics; elastomers, for example, butadiene/styrene copolymers and butadiene/acrylonitrile copolymers; terpolymers of acrylonitrile, butadiene, and styrene; natural rubber; butyl rubber; and polysiloxanes. The polymer may also be a blend of various polymers. Further, the polymer may be, where appropriate, cross-linked by chemical means or by irradiation. Its incorporation into these substances may be carried out by any known method at doses ranging from about 5 to about 40% relative to the weight of the inflammable substance.

The following Examples illustrate the process of this invention and are not to be taken as limiting the scope of the invention.

EXAMPLE I

Preparation of N,N'-Bis(Tetrabromophthalimide)

This Example is not of this invention but was run to provide a base line for comparison. Into a one-liter resin kettle was charged 481.0 g of Saytex RB-49 flame retardant (tetrabromophthalic anhydride) and 506 g of 96.7% sulfuric acid. The resultant solution was stirred with an overhead stirrer and heated to 100° C.

Into a 500 mL Erlenmeyer flask was charged 102.8 g hydrazine sulfate and 706 g of 96.7% sulfuric acid. The flask contents were heated and stirred until all of the hydrazine sulfate was dissolved.

The hydrazine sulfate solution was then added dropwise to the resin kettle with a polyethylene pipet over a period of sixty-five minutes to form a reaction mass.

The resulting reaction mass was stirred and heated to 180° C. for 14 hours. The reaction mass was allowed to cool and then subjected to vacuum filtration using a 3-liter funnel (90° C. glass frit) to remove the sulfuric acid. The filter cake was then scraped into a 4-liter beaker containing 3 liters of ice water. The mixture was stirred, allowed to settle, and decanted. The filter cake was returned to the 3-liter funnel, washed and filtered until the supernatant water had a neutral pH. The filter cake was then placed in a large crystallizing dish and dried at 100° C. under vacuum for 24 hours to give 449.5 g of a white solid (94% yield) that had a melting point >500° C. Thermogravimetric Analysis (TGA) was used to determine the purity of the solid as 95% N,N'-bis(tetrabromophthalimide).

EXAMPLE II

A batch of N,N'-bis(tetrabromophalimide) was produced by the general procedure of Example I except that the product was treated before drying. The wet filter cake containing sulfuric acid was split into two fractions. One fraction was washed with water. The dry cake from the fraction washed with water had an acid number of 1.28 mg KOH/g and contained 92% N,N-bis(tetrabromophthalimide). The second fraction was washed with water, then treated with a 5% NaOH solution followed by a water wash. The dry cake from the second fraction had an acid number of 0.77 mg KOH/g, and contained 94% N,N'-bis(tetrabromophthalimide). A comparison of the properties of the two fractions is contained in Table 1.

TABLE 1

| Fraction | Acid No. (mg KOH/g) | Mean Particle Size (μ) | 99% less than (μ) | TGA % Wt Loss up to 300° C. | TGA wt % Bisimide |
| --- | --- | --- | --- | --- | --- |
| Water Washed | 1.28 | 7.73 | — | 3.8 | 92 |
| Treated | 0.77 | 5.44 | — | 1.6 | 94 |

EXAMPLE III

A batch of N,N'-bis(tetrabromophthalimide) was produced by the general procedure of Example I except that the product was treated before drying. As in Example II, the wet filter cake containing sulfuric acid was split into two fractions. One fraction was washed with water. The dry cake from the fraction washed with water had an acid number of 2.15 mg KOH per gram and contained 94% N,N'-bis(tetrabromophthalimide). The second fraction was washed with water, then treated with an ammonium hydroxide solution followed by a water rinse. The acid number of the second fraction was 0.26 mg KOH per gram and contained 96% N,N'-bis(tetrabromophthalimide). A comparison of the properties of the two fractions is contained in Table 2.

TABLE 2

| Fraction | Acid No. (mg KOH/g) | Mean Particle Size (μ) | 99% less than (μ) | TGA % Wt Loss up to 300° C. | TGA wt % Bisimide |
| --- | --- | --- | --- | --- | --- |
| Water Washed | 2.15 | 5.64 | 25.9 | 3.4 | 94 |
| Treated | 0.26 | 4.94 | 15.6 | 0.8 | 96 |

EXAMPLE IV

Following the general procedure of Example I, a batch of N,N'-bis(tetrabromophthalimide) was prepared. The dried product contained 86% N,N'-bis(tetrabromophthalimide) and had an acid number of 1.65 mg KOH per gram. One fraction of the dry product was slurried in water and the slurry was fed to a centrifuge. The solids were treated while in the centrifuge with an ammonium hydroxide solution and then washed with water. After drying this fraction, the product contained 95% N,N'-bis(tetrabromophthalimide) and had a acid number of 0.29 mg KOH per gram. A comparison of the treated and untreated product is contained in Table 3.

TABLE 3

| Fraction | Acid No. (mg KOH/g) | Mean Particle Size (μ) | 99% less than (μ) | TGA % Wt Loss up to 300° C. | TGA wt % Bisimide |
| --- | --- | --- | --- | --- | --- |
| Untreated | 1.65 | 23.0 | 85.1 | 10.6 | 86 |
| Treated | 0.290 | 12.35 | 43.25 | 1.5 | 95 |

EXAMPLE V

Following the general procedure of Example I, a batch of N,N'-bis(tetrabromophthalimide) was prepared. Prior to separation of the bisimide product from the reaction mass, a portion of the product was treated by adding a solution of NH$_4$OH to the reaction mass to neutralize the sulfuric acid. After obtaining a neutral mixture, an additional amount of NH$_4$OH was added to the reaction mass so as to obtain a slightly basic solution. The other portion was washed with water but not treated. Both portions were then filtered separately, rinsed with water and then dried. Table 4 illustrates a comparison of the treated and untreated products.

TABLE 4

| Fraction | Acid No. (mg KOH/g) | Mean Particle Size (μ) | 99% less than (μ) | TGA % Wt Loss up to 300° C. | TGA wt % Bisimide |
| --- | --- | --- | --- | --- | --- |
| Water Washed | 1.11 | 6.36 | 26.14 | 2.4 | 94 |
| Treated | 0.14 | 5.56 | 15.17 | 1.6 | 95 |

EXAMPLE VI

Following the general procedure of Example I, a batch of N,N'-bis(tetrabromophthalimide) was prepared. The batch was split into two fractions. The first fraction was water washed and dried while the second fraction was treated with an NH$_4$OH solution during the centrifugation. Table 5 illustrates the characteristics of each fraction of the batch.

TABLE 5

| Fraction | Acid No. (mg KOH/g) | Mean Particle Size (μ) | 99% less than (μ) | TGA % Wt Loss up to 300° C. | TGA wt % Bisimide |
| --- | --- | --- | --- | --- | --- |
| Water Washed | 1.773 | 3.16 | 10.47 | 5.1 | 91.8 |
| Treated | 0.353 | 2.59 | 6.61 | 0.5 | 96.8 |

The bisimide products of this invention have an excellent white color, which color is advantageous when the products are used in producing articles which are of a light color or which are white.

We claim:

1. The process for preparing a product in N,N'-bis-(tetrabromophthalimide), which process comprises:
   (a) forming a reaction mass from at least (i) tetrabromophthalic anhydride, (ii) hydrazine or a hydrazine providing compound, and (iii) a reaction medium;
   (b) maintaining the so-formed reaction mass at a temperature within the range of from about 40° C. to about 300° C. for a time sufficient to obtain a product predominant in N,N'-bis(tetrabromophthalimide);
   (c) separating the product from the reaction mass;
   (d) contacting the separated product with an aqueous basic solution; and
   (e) recovering the contacted product, said contacted product being comprised of a predominant amount of N,N'-bis(tetrabromophthalimide) and minor amounts of impurities which comprise tetrabromophthalate anhydride and N-aminoimide wherein the molar ratio of the N-aminoimide to tetrabromophthalate anhydride is within the range of from about 1.5:1 to about 100:1.

2. The process of claim 1 wherein the molar ratio of N-aminoimide to tetrabromophthalic anhydride is within the range of from about 2:1 to about 1:1.

3. The process of claim 1 wherein the reaction mass is maintained at a temperature within the range of from about 110° C. to about 300° C.

4. The process of claim 1 wherein the reaction medium is concentrated sulfuric acid or oleium.

5. The process of claim 4 wherein said hydrazine is provided as a solution of hydrazine sulfate in concentrated sulfuric acid.

6. The process of claim 4 wherein the concentrated sulfuric acid is from about 90% to about 100% sulfuric acid in aqueous solution.

7. The process of claim 4 wherein the reaction mass is maintained at a temperature within the range of from about 110° C. to about 300° C.

8. The process of claim 4 wherein the molar ratio of N-aminoimide to tetrabromophthalic anhydride is within the range of from about 2:1 to about 10:1.

9. The process of claim 1 wherein the reaction mass is formed from about 1.67 to about 1.25 moles of tetrabromophthalic anhydride per mole of hydrazine or hydrazine providing compound used in forming the reaction mass.

10. The process of claim 1 wherein said period of time is up to about 20 hours.

11. The process of claim 1 wherein the aqueous basic solution is a NaOH, a KOH, an $NH_4OH$, or a $Na_2CO_3$ solution.

12. The process of claim 1 wherein the so contacted product is recovered by centrifugation.

13. The process of claim 1 further comprising washing the separated product from step (c) prior to step (d).

* * * * *